US005639758A

United States Patent [19]
Sharpe et al.

[11] Patent Number: 5,639,758
[45] Date of Patent: Jun. 17, 1997

[54] TOPICAL APPLICATION OF SPIPERONE OR DERIVATIVES THEREOF FOR TREATMENT OF PATHOLOGICAL CONDITIONS ASSOCIATED WITH IMMUNE RESPONSES

[75] Inventors: Richard J. Sharpe, Gloucester; Kenneth A. Arndt, Newton Centre; Stephen J. Galli, Winchester, all of Mass.

[73] Assignee: Beth Israel Deaconess Medical Center, Inc., Boston, Mass.

[21] Appl. No.: 120,218

[22] Filed: Sep. 13, 1993

Related U.S. Application Data

[63] Continuation of Ser. No. 831,429, Feb. 5, 1992, Pat. No. 5,244,902, which is a continuation-in-part of Ser. No. 494,744, Mar. 16, 1990, abandoned, which is a continuation-in-part of Ser. No. 396,523, Aug. 21, 1989, abandoned.

[51] Int. Cl.$^6$ .................................................. A61K 31/445
[52] U.S. Cl. .............................................. 514/278; 514/885
[58] Field of Search ........................................ 514/278, 885

[56] References Cited

U.S. PATENT DOCUMENTS

| | | | |
|---|---|---|---|
| 2,788,309 | 4/1957 | Cooper | 514/280 |
| 2,854,380 | 9/1958 | Jensen | 514/280 |
| 3,155,669 | 11/1964 | Janssen et al. | 546/20 |
| 3,155,670 | 11/1964 | Janssen et al. | 546/20 |
| 3,161,644 | 12/1964 | Janssen et al. | 546/215 |
| 3,238,216 | 3/1966 | Janssen et al. | 546/20 |
| 3,996,363 | 12/1976 | Wade et al. | 514/278 |
| 4,839,342 | 6/1989 | Kaswan | 514/11 |
| 4,874,766 | 10/1989 | Ooms et al. | 514/258 |

FOREIGN PATENT DOCUMENTS

| | | |
|---|---|---|
| 633914 | 12/1963 | Belgium . |
| 2163717 | 7/1973 | France . |

OTHER PUBLICATIONS

Blozyski, et al., Arch. Intern, Pharmacodynamie, 123, 58–66 (1959), Chemical Abstracts, 54, Abstract 215049–i (1960).

Burka, et al., "Dopaminergic (Co–Mediator) Modulation of Release of Histamine and SRS–A in the Calf," British Journal of *Pharmacology*, 58(3) 445 (1976).

Eyre, "Dopamine Potentiates Anaphylactic Contraction of Pulmonary Vein of Calf," *Research Communications in Chemical Pathology and Pharmacology*, 22(3) 447–453 (1978).

Levsen et al., "Receptor Binding of R 41 468, A Novel Antagonist at 5–HT2 Receptors," *Life Sciences*, 28(9) 1015–1022 (1981).

Moerlein et al, "Effect of Lipophilicity on the In Vivo Localization of Radiolabelled Spiperone Analogues", *Int. J. Nucl. Med. Biol.* 12, 353–56 (1985).

Nakanishi, M., et al., "Spirohydantion Derivataives," *Chemical Abstracts* vol. 75 (1971) 110315n.

Reynolds, "Martindale, The Extra Pharmacopoeia," The Pharmaceutical Press, London, 1989.

*Primary Examiner*—José G. Dees
*Assistant Examiner*—Mary C. Cebulak
*Attorney, Agent, or Firm*—Kilpatrick & Cody, L.L.P.; Roy D. Meredith

[57] ABSTRACT

A method for the treatment of a cutaneous, ocular, or mucosal pathological condition which is associated with immune response in a human or other mammal, that includes topical application of an effective amount of spiperone or a spiperone derivative or its pharmaceutically acceptable salt, in a pharmaceutically-acceptable diluent or carrier for topical application.

3 Claims, 7 Drawing Sheets

TOPICAL APPLICATION OF SPIPERONE OR DERIVATIVES THEREOF FOR TREATMENT OF PATHOLOGICAL CONDITIONS ASSOCIATED WITH IMMUNE RESPONSES

This is a continuation of application Ser. No. 07/831,429 filed in the U.S. Patent & Trademark Office on Feb. 5, 1992, now U.S. Pat. No. 5,244,902, which is a continuation-in-part of U.S. Ser. No. 07/494,744, now abandoned filed on Mar. 16, 1990, which is a continuation-in-part of U.S. Ser. No. 07/396,523, filed on Aug. 21, 1989, now abandoned.

BACKGROUND OF THE INVENTION

This invention is in the area of the topical treatment of cutaneous, ocular, and mucosal hypersensitivity and hyperproliferative conditions induced by or associated with an immune response, that includes the application of an effective amount of spiperone or a spiperone derivative, or a pharmaceutically acceptable salt thereof, in a pharmaceutically acceptable carrier.

The immune system specifically recognizes and selectively eliminates foreign invaders, or other antigenic agents, by a process known as the immune response. The immune response has three major characteristics: it responds adaptively to foreign invaders, it exhibits strong specificity, and it displays a long-term memory of earlier contacts with specific foreign pathogens or antigens. The immune response involves the production of antibody and/or the destruction of antigenic cells by lymphocytes, which are highly specific for the antigen or hapten.

When directed against an infectious organism, the immune response can provide great benefit to the host. As an example, an important component of current public health practices is the use of vaccines to elicit immune responses against infectious organisms that cause severe illness and death. However, when directed against agents that are relatively innocuous, such as pollen, animal dander, and certain plant resins, damage to the host's tissues that is out of proportion to any threat to health posed by the antigenic agent that elicited the response can be caused by cells, antibodies, and mediators which represent the effector components of the immune response.

For example, cutaneous contact hypersensitivity responses are complex expressions of a cellular immune response characterized by antigen-dependent changes in lymphocyte traffic, the recruitment of circulating leukocytes to the site of antigen challenge (leukocyte infiltration) and alterations in vascular permeability and blood flow resulting in tissue swelling (edema). In humans and companion animals, cutaneous contact hypersensitivity responses can occur on exposure to certain plant resins, such as those of poison ivy, and other commonly encountered agents in the environment. In individuals sensitized to such commonly encountered agents, a severe contact reaction can result upon exposure, with significant associated morbidity. Severe or repeated contact hypersensitivity reactions can be followed by significant chronic changes, such as scarring of affected tissues, itchiness, swelling, scaling and oozing of tissue fluid through the skin surface. This pathology may predispose the patient to bacterial superinfection. In the eye, chronic immune responses can lead to diminished vision or actual blindness. In the lung, chronic immune responses, such as chronic allergic asthma, can result in serious chronic lung disease.

Cutaneous contact hypersensitivity and asthma are just two examples of immune responses that can be associated with significant morbidity. Others include atopic dermatitis, eczema, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, lichen planus, asthma, allergic asthma, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Similarly, psoriasis, a common cutaneous disease associated with a hyperproliferating epidermis, also has a leukocyte infiltration component. Immunologically mediated leukocyte infiltration also occurs at sites other than the skin, such as in the airways in asthma and in the tear producing gland of the eye in keratoconjunctivitis sicca.

It is now believed that leukocytes and other cells found in the normal and abnormal skin, eye, or mucosal membranes secrete a variety of cytokines. During immunological responses affecting these sites, cytokines are important in recruiting additional leukocytes into these tissues, in promoting epithelial hyperproliferation, and in inducing other chronic changes such as scarring. For example, eosinophils, a type of granulocyte found in many pathological immune responses including atopic dermatitis and asthma, can product the cytokine TGF-$\alpha$ (Wong D. T. W., Weller P. F., Galli, S. J., Elovic A., Rand, T. H., Gallagher, G. T., Chiang, T., Chou, M. Y., Matossian, K., McBride, J., Todd, R. Human eosinophils express transforming growth factor-alpha. *J. Exp. med.* 1990; 172:673–81), which promotes epithelial hyperproliferation, and TGF-$\beta$ (Wong, D. T. W., Elovic, A., Matossian, K., Nagura, N., McBride, J., Chou, M. Y., Gordon, J. R., Rand, T. H., Galli, S. J., Weller, P. F. Eosinophils from patients with blood eosinophilia express transforming growth factor $\beta$1. *Blood* 1991; 78:2702–2707), which promotes fibrosis.

In addition to disorders that clearly represent pathological consequences of immune responses, immune responses are thought to contribute to many other pathological conditions, including Crohn's disease and ulcerative colitis of the gastrointestinal tract, psoriasis, alopecia areata and others. While the cause of most of these disorders is unclear, it is thought that exogenous agents yet to be defined or components of the host's own tissues (in the case of autoimmune disorders) may provoke an immune response that is responsible for the infiltration of lymphocytes, monocytes, and granulocytes observed in these conditions. It is also believed that the infiltrating cells significantly contribute to the tissue pathology associated with these disorders, through the production of cytokines as well as other mechanisms.

The need to control the wide variety of pathological responses with immunological components which result in cutaneous, ocular, or mucosal hypersensitivity reactions, hyperproliferation, and scarring has led to a search for effective therapeutic agents that are both safe and effective.

Because of the importance of leukocytes and their products in the development of pathology associated with immune responses, many approaches to treating these conditions are focused on inhibiting the immune responses and leukocyte infiltration contributing to these disorders. Several substances are known to be able to inhibit the immune responses contributing to cutaneous leukocyte responses or hyperproliferative responses. Corticosteroids, when administered systemically, are effective in this regard but are associated with significant and potentially dangerous side effects. Topically applied corticosteroids have some efficacy in treating these conditions, but are only partially effective in many instances and have their own significant side effects, including atrophy of tissue, formation of telangiectasia, blanching, and a myriad of systemic effects if significantly absorbed. Other agents with partial utility for treating some of the above conditions include psoralen plus ultraviolet A (PUVA), cyclosporin A, or azathioprine, but the risk-to-benefit ratios for these agents is unfavorable for most of the conditions described above.

As a result, there is a significant and very longstanding need to identify new agents with favorable benefit to risk ratios that can be applied topically to prevent or suppress (i.e. "treat") immune responses contributing to cutaneous, ocular, or mucosal hypersensitivity reactions, hyperproliferation, or scarring. Optimally, such agents should be effective when applied locally, and systemic absorption should not result in blood levels high enough to cause significant systemic toxicity or other adverse side effects. Not only does local administration place the agent in closest contact with the site needing treatment, but it also diminishes the possibility that such treatment will suppress beneficial immune responses which may occur at other, more distant, sites.

In contrast to the immune response, an inflammatory response is a pathologic condition that can occur in response to immunologically non-specific injury, either from physical (such as trauma), chemical, or biologic agents. An inflammatory response is characterized by increased blood flow and redness in the inflamed area, increased capillary permeability and edema, and recruitment of immunologically non-specific white blood cells, especially neutrophils, that remove injurious material and promote repair. Unlike immune responses, inflammatory responses do not respond adaptively to the inciting stimulus, do not show specificity and do not exhibit long term memory. Cellular products of lymphocytes may contribute to or induce an inflammatory response. However, because of the differences in mechanisms, a compound can function as an anti-inflammatory agent without having immunosuppressive properties. Phenylbutazone, indomethacin, aspirin, ibuprofen, and acetaminophen are examples of anti-inflammatory compounds which have no significant immunosuppressive activity, as demonstrated by their lack of a significant effect on immunologically mediated responses, such as contact hypersensitivity. U.S. Pat. No. 3,996,363 to Wade discloses that certain naphthalimide derivatives of spiperone have anti-inflammatory activity.

Spiperone (8-[3-{p-fluorobenzoyl}propyl]-1-propyl]-1-phenyl-1,3,8-triazaspiro-[4.5]decan-4-one) is a neuroleptic agent with central nervous system (CNS) dopamine and serotonin (5-HT) receptor antagonist properties. Some analogues of spiperone are useful as experimental reagents in dopamine and serotonin receptor studies. For example, the high affinity of an immobilized spiperone derivative, 3-(2-aminoethyl)-8-[3-(4-fluorobenzoyl)propyl]-4-oxo-1-phenyl-1,3,8-triazaspiro[4.5]decan-4-one trihydrochloride, for dopamine receptors has made it possible to isolate these receptors in pure form. Radiopharmaceuticals based on spiperone and its analogues have been shown to be useful in assessing dopamine receptor function based on positron emission tomography (PET) in animals and man. Spiperone has also been shown to bind to human and mouse lymphocytes, although the mechanism responsible for such binding is uncertain.

U.S. Pat. No. 4,874,766 assigned to Janssen Pharmaceutica N.V. discloses a method for promoting wound-healing by topical administration of a serotonin-antagonist compound, including spiperone and its derivatives. Wound healing is a reparative process by which several types of resident cells, such as epithelial cells, fibroblasts and vascular endothelial cells, and certain circulating cells, including neutrophils, lymphocytes and macrophages, act in concert to restore to a more healthy condition tissues that have sustained various forms of mechanical or other injury. Although lymphocytes and macrophages participate in both wound healing and in immune responses, the specific roles of these cells in the two types of processes may be distinct. In fact, treatment of wounds with immunosuppressive agents, such as corticosteroids and cyclosporin A, has been known to cause impairment of the healing process (*Arch Surg* May 1990, 125(5), 636–40; *Ann Ophthamol.* April 1985; 17(4), 238, and *J. Surg. Res.* June 1983; 34(6), 572–5).

It is an object of the present invention to present a method for the topical treatment of cutaneous, mucosal and ocular pathology associated with immune responses.

It is yet another object of the present invention to present a method for the topical treatment of cutaneous, mucosal, or ocular hypersensitivity and epithelial hyperproliferation.

It is yet another object of the invention to present a method for the topical treatment of cutaneous, mucosal or ocular scarring.

SUMMARY OF THE INVENTION

A method for the treatment of a cutaneous, ocular, or mucosal condition in a human or other mammal resulting from pathology associated with an immune response, that includes topical application of an effective amount of spiperone or a spiperone derivative or its pharmaceutically acceptable salt, in a pharmaceutically-acceptable diluent or carrier for topical application.

It has been discovered that the parent spiperone exhibits a strong immunosuppressive activity when applied topically. The parent spiperone is used herein as the model of an active topical immunosuppressant. Spiperone derivatives are measured against this model, and are considered to be immunosuppressants if they suppress the leukocyte infiltration and/or the ear swelling associated with an experimental contact hypersensitivity response by at least 40% at 24 hours after specific antigen challenge.

In the preferred method of administration, the active compounds are administered topically in a suitable carrier to effectively immunosuppress the patient at the site of application. Because the application is topical, i.e., local, immunosuppression is achieved without producing systemic effects, most notably, the significant neuroleptic effect that is associated with the systemic administration of spiperone.

Spiperone and its active derivatives are useful as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides. These compounds can also be used to treat an aqueous-deficient dry eye state (such as immune mediated keratoconjunctivitis) in a patient suffering therefrom, by administering the compound topically to the eye.

BRIEF DESCRIPTION OF THE FIGURES

In FIG. 8a, the slight effect of treatment of the right ears with spiperone on reactions expressed in the left ears of the same mice was not significant (p>0.05).

DETAILED DESCRIPTION OF THE INVENTION

Definitions

As used herein, the term "spiperone" refers to the compound (8-[3-{p-fluorobenzoyl}propyl]-1-propyl]-1-phenyl-1,3,8-triazaspiro-[4.5]decan-4-one).

As used herein, the term "spiperone derivative" refers to a molecule (1) that contains the spiperone nucleus:

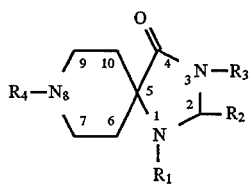

wherein $R_1=CH_3-$, $C_6H_5-$, cyclohexyl, $4-(OCH_3)C_6H_4-$, $3-(CH_3)C_6H_4-$, $4-(CH_3)C_6H_4-$, $4-X-C_6H_4-$, $(CH_3)_2CH-$, $CH_3(CH_2)_3-$, $(CH_3)_2CHCH_2-$, $CH_3CH_2CH(CH_3)-$, $(CH_3)_3C-$; or $Y-CH_2(CH_2)_m-$.

$R_2=H$ or $CH_3$;

$R_3=H$, $CH_3$, $CH_3CH_2-$, $CH_3CH_2CH_2-$, $(CH_3)_2CH-$, $CN(CH_2)_2-$, or $CH_3(CH_2)_s-$;

$R_4=H$, $C_6H_5CH(CH_2CH_3)CH_2-$, $C_6H_5CH(CH_3)(CH_2)_2-$, $C_6H_5CH_2CH(CH_3)CH_2-$, $C_6H_5CH_2CH_2CH(CH_3)-$, $C_6H_5CH(CH_3)(CH_2)_3-$, $4-CH_3C_6H_4CH(CH_3)(CH_2)_3-$, $4-(CH_3O)C_6H_4CH(CH_3)(CH_2)_3$, $4-X-C_6H_4CH(CH_3)CH_2-$, $4-X-C_6H_4CH(CH_2CH_3)CH_2-$, $4-X-C_6H_4CH(CH_3)(CH_2)_2-$, $4-X-C_6H_4-CH(CH_3)(CH_2)_3-$, $C_6H_5CH(OCH_3)(CH_2)_2-$.

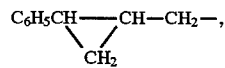

$C_6H_5CO(CH_2)_3-$, $C_6H_5CO(CH_2)_4-$, $4-(CH_3)C_6H_4CO(CH_2)_3-$, $4-(CH_3O)C_6H_4CO(CH_2)_3-$, $4-X-C_6H_4CO(CH_2)_3-$, $4-X-C_6H_4CO(CH_2)_3-$, 2-thienyl-$CO(CH_2)_3-$,

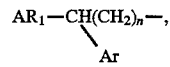

$4-XC_6H_4C(CH_3)CH(CH_2)_2-$, where the configuration about the double bond is cis or trans, $4-XC_6H_4C(CH_3)CHCH_2-$, where the configuration about the double bond is cis or trans, $4-X-C_6H_4COCH=CHCH_2-$, or $Y-CH_2(CH_2)_s-$.

wherein $n=3$ or $4$; m is between 1 to 4; s is between 1 to 6; X=H or is a heteroatom or a substituted heteroatom such as F, Cl, Br, I, $OCH_3$, $SO_3^-$, or $NH_2$; Y=H or a heteroatom such as F, Cl, Br, I, $SO_3$, $PO_4^=$, OH, SH, $SCH_3$, $CH_3SO_2^-$, $NH_2$, $-CO_2^-$; and each of Ar and $Ar_1$ is, independently, H, $C_6H_5-$, $4-(CH_3)C_6H_4-$, $4-(CH_3O)C_6H_4-$, $4-X-C_6H_4-$, $3-(CH_3)C_6H_4-$, 2-thienyl, or $4-X-C_6H_4CH_2-$;

and (2) exhibits an immunosuppressive effect when provided topically, as measured using the assay set out in Example 1, i.e., they suppress the leukocyte infiltrate and/or the ear swelling associated with an experimental contact hypersensitivity response by at least 40% at 24 hours after specific antigen challenge, or as evaluated in vivo in humans by the agent's ability to inhibit contact hypersensitivity responses to patch test allergens in patients hypersensitive to a given allergen, using procedures generally accepted by those of skill in the art.

Figure 3:
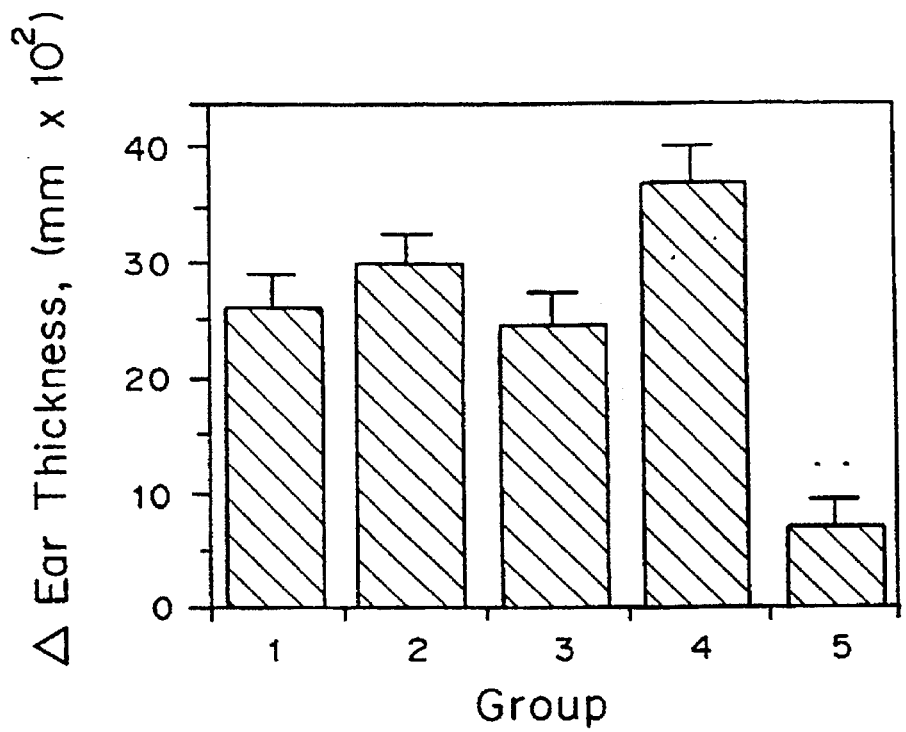
FIG. 3—Comparative effects of systemic vehicle (1), haloperidol (2), trazadone (3), mianserin (4) or spiperone (5) (all agents at 40 mg/kg, subcutaneously) on the tissue swelling associated with oxazolone-induced cutaneous contact hypersensitivity reactions. Spiperone, the other agents, or vehicle alone were administered to BALB/c mice 1 hour after challenge for contact hypersensitivity. The change in ear thickness (post-challenge value minus baseline pre-challenge value) was measured 24 hours after oxazolone challenge. The data are presented as the mean ±SEM. The reduction in ear swelling observed with spiperone was significant when compared to the reactions observed in the control, vehicle treated animals (**=p<0.01), whereas haloperidol, trazadone and mianserin did not significantly suppress the tissue swelling associated with contact hypersensitivity.
Figure 4:
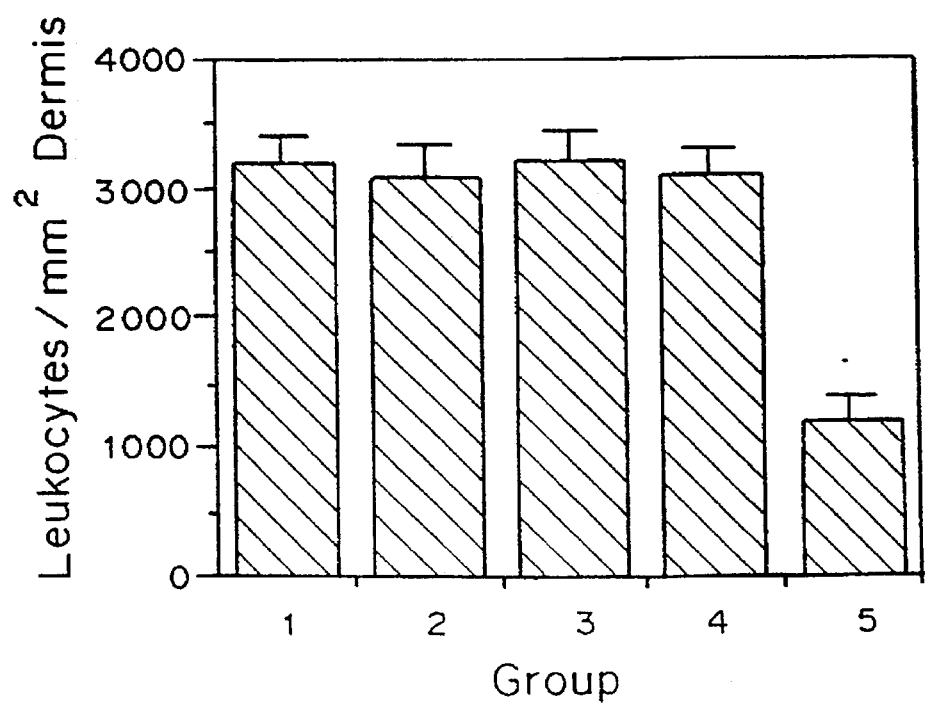
FIG. 4—Comparative effects of systemic treatment with vehicle (1) or haloperidol (2), trazadone (3), mianserin (4) or spiperone (5) (all agents at 40 mg/kg), administered subcutaneously, on leukocyte infiltration associated with 24-hour contact hypersensitivity reactions. These data (mean ±SEM) are derived from the same mice whose ear thickness values are shown in FIG. 3. The reduction in leukocyte infiltration observed in animals treated with spiperone was significant when compared to the reactions observed in animals treated with vehicle alone (*p<0.05), while haloperidol, trazadone and mianserin did not significantly suppress the leukocyte infiltration associated with contact hypersensitivity.

As illustrated in FIGS. 3 and 4, the chemically unrelated serotonin receptor antagonists, trazadone and mianserin, and the dopamine receptor antagonist, haloperidol, are not effective in suppressing contact hypersensitivity. On this basis, it is clear that the mechanism of action of spiperone and spiperone derivatives in suppressing the immune response is independent of their serotonin or dopamine receptor blocking properties.

I. Structure and Synthesis of Spiperone Derivatives

The parent spiperone is 8-[3-(p-fluorobenzoyl)propyl]-1-phenyl-1,3,8-triazaspiro[4.5]decan-4-one, which has the structure illustrated below.

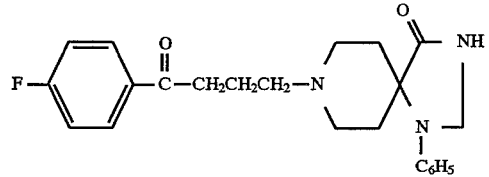

As demonstrated in Example 1, the parent spiperone has significant immunosuppressive activity when applied topically. The potential utility of any one of the above-described spiperone derivatives to act as an immunosuppressant can be conveniently determined by synthesizing the compound and testing it in the biological assay described in Example 1.

Those derivatives of spiperone which are particularly useful in the method of the invention are those which have decreased affinities for dopamine and/or serotonin receptors, but which obtain immune suppressive properties.

Methods of synthesis of spiperone derivatives are disclosed in, or can be easily adapted from syntheses disclosed in, U.S. Pat. Nos. 3,155,669; 3,155,670; 3,161,644; and 3,238,216; all of which are hereby incorporated by reference.

III. Therapeutic Compositions

Mammals, and specifically humans, suffering from pathogenic cutaneous, ocular, or mucosal immune responses can be treated by topical administration to the patient of an effective amount of the spiperone derivative or its salt in the presence of a pharmaceutically acceptable carrier or diluent.

The active compound is administered topically in an effective dosage range to cause immunosuppression of the target pathogenic immune response. The active compound is included in the pharmaceutically acceptable carrier or diluent in an amount sufficient to deliver to a patient a therapeutic amount of the spiperone derivative in vivo in the absence of serious toxic effects. In general, local immunosuppression can be achieved by topically administering lower doses of spiperone derivatives than would be required if the agents were administered systemically.

A typical daily dose of active compound is between 0.1 milligrams and 120 grams. The active compounds can be applied in any effective concentration, usually varying between 0.001% and 50% (all percentages are by weight).

Spiperone or its derivative is administered for a sufficient time period to alleviate the undesired symptoms and the clinical signs associated with the condition being treated. The concentration of active compound in the drug composition will depend on absorption, inactivation, and other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

The spiperone derivative can be mixed with other active materials which do not impair the desired action, or with materials that supplement the desired action, such as antibiotics, antifungals, anti-inflammatories, antivirals, or other immunosuppressive agents.

Solutions or suspensions for topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Suitable vehicles or carriers for topical application are known, and include lotions, suspensions, ointments, creams, gels, tinctures, sprays, powders, pastes, slow-release transdermal patches, aerosols for asthma, suppositories for application to rectal, vaginal, nasal or oral mucosa, mouthwashes, or swish and spit preparations.

Thickening agents, emollients, and stabilizers can be used to prepare topical compositions. Examples of thickening agents include petrolatum, beeswax, xanthan gum, or polyethylene glycol, humectants such as sorbitol, emollients such as mineral oil, lanolin and its derivatives, or squalene. A number of solutions and ointments are commercially available, especially for ophthalmic and dermatologic applications.

Natural or artificial flavorings or sweeteners can be added to enhance the taste of topical preparations applied for local effect to mucosal surfaces. Inert dyes or colors can be added, particularly in the case of preparations designed for application to oral mucosal surfaces.

Spiperone or its derivative can be applied in a time release formulation via patches or by slow release polymers. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. The materials can also be obtained commercially from Alza Corporation and Nova Pharmaceuticals, Inc.

Spiperone or its derivatives can be provided in the form of pharmaceutically-acceptable salts. As used herein, the term "pharmaceutically-acceptable salts or complexes" refers to salts or complexes that retain the desired biological activity of the parent compound and exhibit minimal, if any, undesired toxicological effects. Examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with polyvalent metal cations such as zinc, calcium, bismuth, barium, magnesium, aluminum, copper, cobalt, nickel, cadmium, and the like, or with an organic cation formed from N,N-dibenzylethylene-diamine or ethylenediamine; or (c) combinations of (a) and (b); e.g., a zinc tannate salt or the like.

The spiperone derivatives can be modified in order to enhance their usefulness as pharmaceutical compositions. For example, it is well know in the art that various modifications of the active molecule, such as alteration of charge, can affect water and lipid solubility and thus alter the potential for percutaneous absorption. The vehicle, or carrier, can also be modified to enhance cutaneous absorption, enhance the reservoir effect, and minimize potential irritancy or neuropharmacological effects of the composition. See, in general, Arndt, K. A., P. V. Mendenhall, "The Pharmacology of Topical Therapy", *Dermatology in General Medicine,* 1987; T. B. Fitzpatrick, A. Z. Eisen, K. Wolff, I. M. Freedberg and K. F. Austen, eds., 3d ed., McGraw Hill, Inc., New York, pp. 2532–2540.

IV. Immunosuppressant Activity of Spiperone Derivatives

Spiperone and spiperone derivatives are capable of suppressing the immune response in humans and other mammals on topical application. As such, the compounds, or therapeutic compositions thereof, are useful for the treatment of a myriad of immunological disorders. Pathogenic immune responses that can be treated by topical application of spiperone or spiperone derivatives include contact dermatitis, atopic dermatitis, eczematous dermatitis, drug eruptions, lichen planus, psoriasis, alopecia areata, Sjogren's Syndrome, including keratoconjunctivitis sicca secondary to Sjogren's Syndrome, cutaneous lupus erythematosus, scleroderma, allergic reactions secondary to arthropod bite reactions, aphthous ulcers, conjunctivitis, keratoconjunctivitis, iritis, asthma and allergic asthma, vaginitis, Crohn's disease, ulcerative colitis and proctitis. These compounds can also be useful in reducing the infiltration of skin by malignant leukocytes in diseases such as mycosis fungoides.

Spiperone and its derivatives can also be used to increase tear production in a patient suffering from deficient tears in the eye due to an autoimmune dysfunction of the lacrimal glands, such as immune mediated keratoconjunctivitis (KCS, or dry eye). Canine KCS is a common, chronic progressive, and potentially blinding disease. A continuum of corneal and conjunctival lesions ensues from the dry eye state. Spiperone or its active derivatives can be provided as an ophthalmic drop or ophthalmic ointment to humans or other mammals, including dogs and cats, in an effective amount in a suitable vehicle. This topical ophthalmic treatment can also serve to correct corneal and conjunctival disorders exacerbated by tear deficiency and KCS, such as corneal scarring, corneal ulceration, filamentary keratitis, mucopurulent discharge, and vascularization of the cornea. Spiperone and its derivatives can also be used to decrease immune responses which contribute to granulation and neovascularation in the cornea.

The ability of spiperone (8-[3-{p-fluorobenzoyl}propyl] -1-phenyl-1,3,8-triazaspiro-[4.5]decan-4-one) to influence the tissue swelling and leukocyte infiltration associated with contact hypersensitivity reactions in mice was evaluated as described in detail in Example 1. The parent spiperone compound was used for the procedure in Example 1 as a model of an active immunosuppressant. Spiperone derivatives can be measured against this model, and are considered active if they suppress the leukocyte infiltrate and/or the swelling response by at least 40% 24 hours after specific antigen challenge.

In the procedure of Example 1, contact hypersensitivity reactions were elicited by applying the haptens oxazolone or dinitrofluorobenzene topically to one or both ears five to eight days after epicutaneous sensitization. When spiperone was given subcutaneously at a dose of 150 mg/kg, 1 hour after challenge with oxazolone, cutaneous contact hypersensitivity to this hapten was almost totally abrogated.

This result indicates that spiperone can virtually eliminate the expression of contact sensitivity in subjects that have previously been sensitized to develop an immunological response by exposure to the agent oxazolone. This test mimicks the common clinical situation in which patients who have developed sensitivity to an agent seek relief from the expression of contact sensitivity in response to subsequent encounters with that agent.

A dose of 40 or 30 mg/kg of spiperone subcutaneously also significantly suppressed the reactions but to a lesser degree than the higher dose. When applied topically, preparations of spiperone significantly suppressed both the tissue swelling and the leukocyte infiltration associated with the elicitation phase of contact hypersensitivity to either oxazolone or dinitrofluorobenzene. Topical treatment with spiperone also suppressed the sensitization phase of contact sensitivity. However, mice treated topically with spiperone, unlike those treated systemically, exhibited no drowsiness or other evidence of central nervous system effects.

Spiperone expresses both serotonin and dopamine receptor antagonist activity. However, unlike spiperone, it was discovered that the chemically unrelated serotonin antagonists, trazadone and mianserin, and the dopamine receptor antagonist, haloperidol, were not effective in suppressing contact hypersensitivity. On the basis of this, it is clear that the mechanism of action of spiperone on the immune response is independent of its serotonin or dopamine receptor blocking properties.

EXAMPLE 1: Inhibition of Induced Contact Hypersensitivity.

Six-to-8-week-old female $C_{57}BL/6J$ or BALB/c mice were obtained from the Jackson Laboratory, Bar Harbor, Me. or from Charles River Laboratories, Kingston Facility, Stoneridge, N.Y., respectively.

Spiperone, mianserin, trazadone, haloperidol and oxazolone were purchased from the Sigma Chemical Co. (St. Louis, Mo.).

Oxazolone-Induced Contact Hypersensitivity—Sensitization and challenge for contact hypersensitivity were performed as follows. The abdomens of the mice were shaved with electric clippers, 50 µl of a 4% (w/w) solution of oxazolone in 4:1 (v:v) acetone:olive oil were applied to the shaved abdomen, and 5 µl of the same solution were applied to each hind footpad. Five to eight days later, the mice were challenged for contact hypersensitivity by applying 10 µl of a 0.5% (w:w) solution of oxazolone in 4:1 (v:v) acetone:olive oil to both the inner and outer surface of the right ear of each mouse (in the case of mice treated systemically with spiperone) or to both ears (in the case of mice treated topically with spiperone).

Dinitrofluorobenzene-Induced Contact Hypersensitivity—Mice were treated in an identical manner as above, except that 0.2% (v:v) 1-fluoro-2,4-dinitrobenzene (DNFB) in acetone was used for both sensitization and elicitation of the contact hypersensitivity response.

Systemic Spiperone Treatment—One hour after the application of oxazolone for elicitation of contact hypersensitivity, mice were treated subcutaneously with spiperone (150 or 30 mg/kg body weight) in 0.1 ml of carrier (Cremophor EL, BASF, Parsippany, N.J.), or with 0.1 ml of carrier alone. In a separate experiment, mice were treated in a similar fashion with 40 mg/kg body weight of trazadone, mianserin, haloperidol, or spiperone in 0.1 ml olive oil or with olive oil alone.

Topical Spiperone Treatment—To test whether spiperone affected the sensitization phase of contact hypersensitivity, 50 µl of 0.08% spiperone in propylene glycol was applied to the shaved abdomens of the mice on days -2, -1, 0, 1 and 2, with the day of oxazolone sensitization being designated day 0. To test the effects of spiperone on the expression of contact hypersensitivity in mice already sensitized to oxazolone; mice were treated with spiperone topically at two hours before or one or twenty-two hours after challenge for contact hypersensitivity, by applying 10 µl of a solution of spiperone in vehicle to both sides of the right ear. In the case of oxazolone-sensitized mice treated one hour after challenge, a 4% (w/w) spiperone suspension in 4:1:5 absolute ethanol:propylene glycol:olive oil was used, while 0.13% (w/w) spiperone solution in Vehicle-N (Neutrogena Corp., Los Angeles, Calif.) was used at the other time points. In the case of the DNFB-sensitized mice, 0.5% (w/w) spiperone in absolute ethanol was used.

Evaluation of Ear Swelling Response—Immediately before and 24 or 46 hours after application of oxazolone or DNFB, ear thicknesses were determined with an engineer's micrometer. The increment (delta) in ear thickness (ear swelling) was calculated as the 24- or 46-hour value minus the baseline (pre-challenge) value and expressed in units of $10^{-2}$ mm. Mice were killed by cervical dislocation after the measurement of 24 or 46-hour ear thickness was obtained, and the ears were processed for histologic examination.

Figure 10:
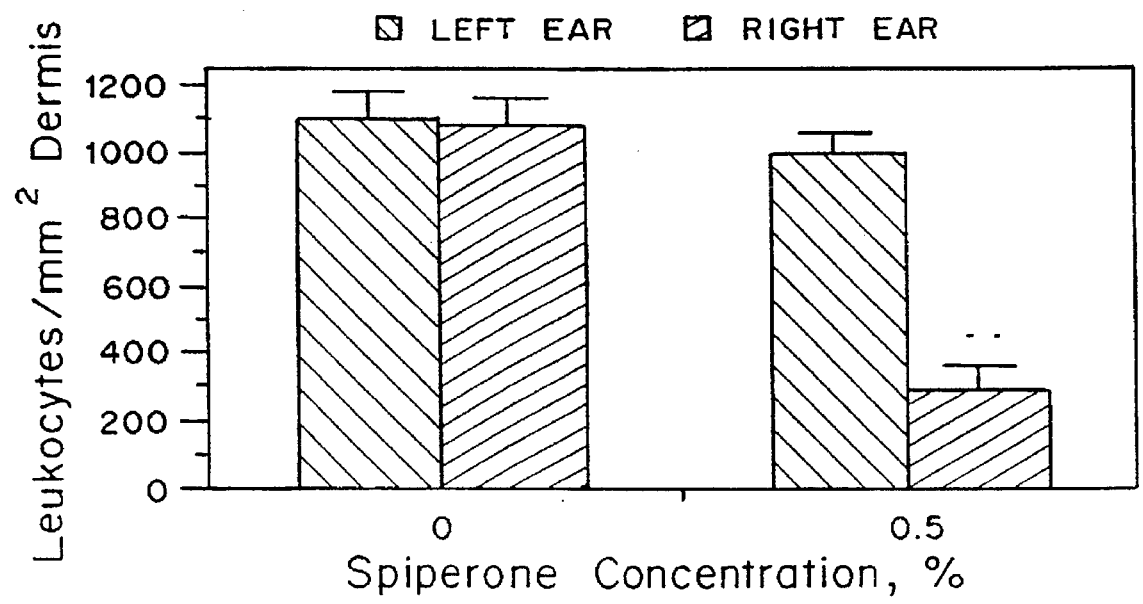
FIG. 10—Effect of topical treatment with spiperone on leukocyte infiltration associated with DNFB-induced contact hypersensitivity reactions. These data (mean ±SEM) are from the same mice whose ear thickness measurements are presented in FIG. 9. Topical treatment with spiperone significantly diminished the reactions when compared to those in vehicle-treated mice (**$p<0.01$). The slight effect of treatment of the right ears with spiperone on reactions expressed in the left ears of the same mice was not significant ($p>0.05$).

Quantification of Leukocyte Infiltration—In most experiments, both ears of each mouse were fixed in 4.0% buffered formalin and then processed routinely and embedded in paraffin for preparation of 6–7 µm-thick hematoxylin and eosin-stained sections. In some experiments (FIGS. 2 and 10), ears were fixed and processed into 1 µm thick, Epon-embedded, Giemsa-stained sections. All of the sections were coded and examined with an ocular grid at 400× under light microscopy by an observer unaware of the identity of the individual slides. The number of leukocytes/ $mm^2$ of dermis was calculated by counting all of the leukocyte cells in an area of at least 0.14 $mm^2$ of dermis.

Statistical Analysis—Differences between groups were assessed by the 2-tailed Student's t test (paired for comparisons of left and right ears in the same mice, unpaired for comparisons between different groups of mice).

Results.

Figure 1:
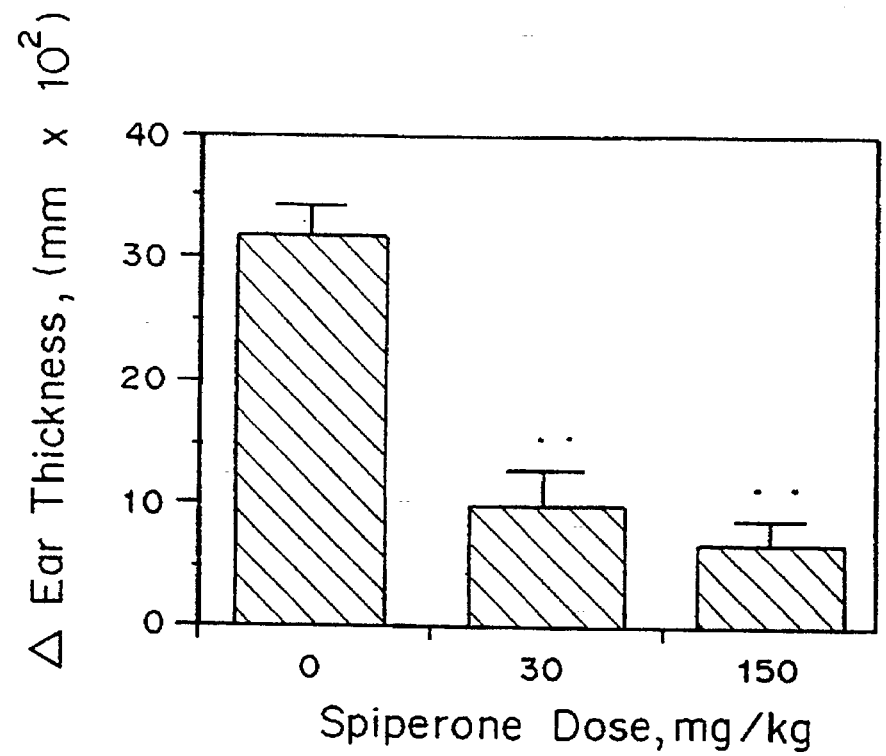
FIG. 1—Effects of systemic spiperone (30 or 150 mg/kg, subcutaneously) on the tissue swelling associated with oxazolone-induced cutaneous contact hypersensitivity reactions. Spiperone or vehicle alone (0) was administered to C57BL/6J mice 1 hour after challenge for contact hypersensitivity. The change in ear thickness (post-challenge value minus baseline pre-challenge value) was measured 24 hours after oxazolone challenge. The data are presented as the mean ±SEM. The reduction in ear swelling observed with either 30 or 150 mg/kg spiperone was significant when compared to the reactions observed in the control animals (**=p<0.01).
Figure 2:
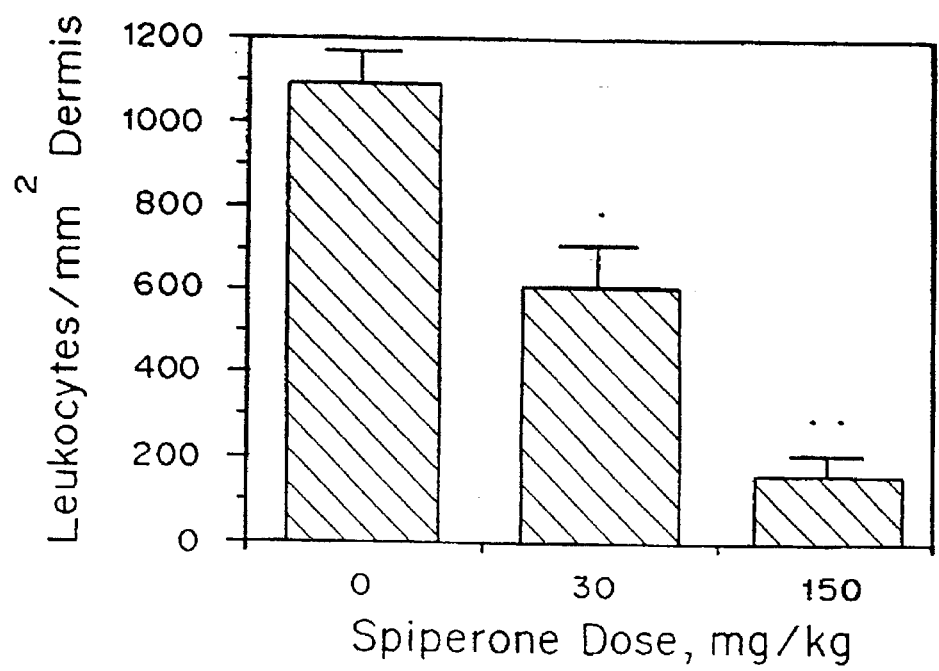
FIG. 2—Effects of systemic treatment with 30 or 150 mg/kg spiperone, subcutaneously, on leukocyte infiltration associated with 24-hour contact hypersensitivity reactions. These data (mean ±SEM) are derived from the same mice whose ear thickness values are shown in FIG. 1. The reduction in leukocyte infiltration observed in animals treated with 30 or 150 mg/kg spiperone was significant when compared to the reactions observed in animals treated with vehicle alone (* or **=p<0.05 or 0.01, respectively).

Effects of Systemic Treatment with Spiperone on Expression of Contact Hypersensitivity—The subcutaneous administration of spiperone at a dose of 150 mg/kg, 1 hour after challenge for contact hypersensitivity to oxazolone, markedly diminished (by 80%) the tissue swelling which developed in association with the contact hypersensitivity response (FIG. 1). FIG. 2 shows that the leukocyte infiltration associated with the response in mice treated with 150 mg/kg spiperone was also diminished by approximately the same amount (81% reduction compared to responses in mice not treated with the drug). However, at this dose, spiperone also produced other remarkable systemic effects. The mice rapidly became lethargic after administration of the drug, and, by 23 hours after spiperone injection, the mice exhibited profound depression of central nervous system function. They appeared to be in a deep sleep, neither ate nor drank, and responded weakly or not at all to touch. They did, however, exhibit responsiveness to pinch.

Some mice were treated with spiperone at 30 mg/kg subcutaneously (FIGS. 1 and 2). At this dose, spiperone diminished the tissue swelling associated with contact hypersensitivity to oxazolone to almost the same extent as did the higher dose (68% reduction with 30 mg/kg versus 80% reduction with 150 mg/kg) but reduced the leukocyte infiltration associated with the reaction by only 37% (FIG. 2). However, the central nervous system effects of spiperone at 30 mg/kg were substantially less pronounced that those observed at the higher dose. Thus, the mice treated with spiperone at 30 mg/kg were less sleepy than those treated with 150 mg/kg. However, the mice treated with 30 mg/kg appeared somewhat lethargic and were less interested in food and water than were control mice treated with carrier alone.

Systemic Spiperone Versus Other Serotonin or Dopamine Receptor Antagonists—In these experiments, systemic spiperone was compared to the serotonin receptor antagonists, trazadone or mianserin, and to the dopamine receptor antagonist, haloperidol, for their ability to inhibit cutaneous contact hypersensitivity. At a dose of 40 mg/kg, only systemic spiperone significantly reduced cutaneous contact hypersensitivity (FIGS. 3, 4). The degree of lethargy in mice treated with 40 mg/kg of spiperone, trazadone, mianserin or haloperidol systemically (FIGS. 1 and 2), appeared to be about the same as that in the mice treated with 30 mg/kg of spiperone systemically.

Figure 5:
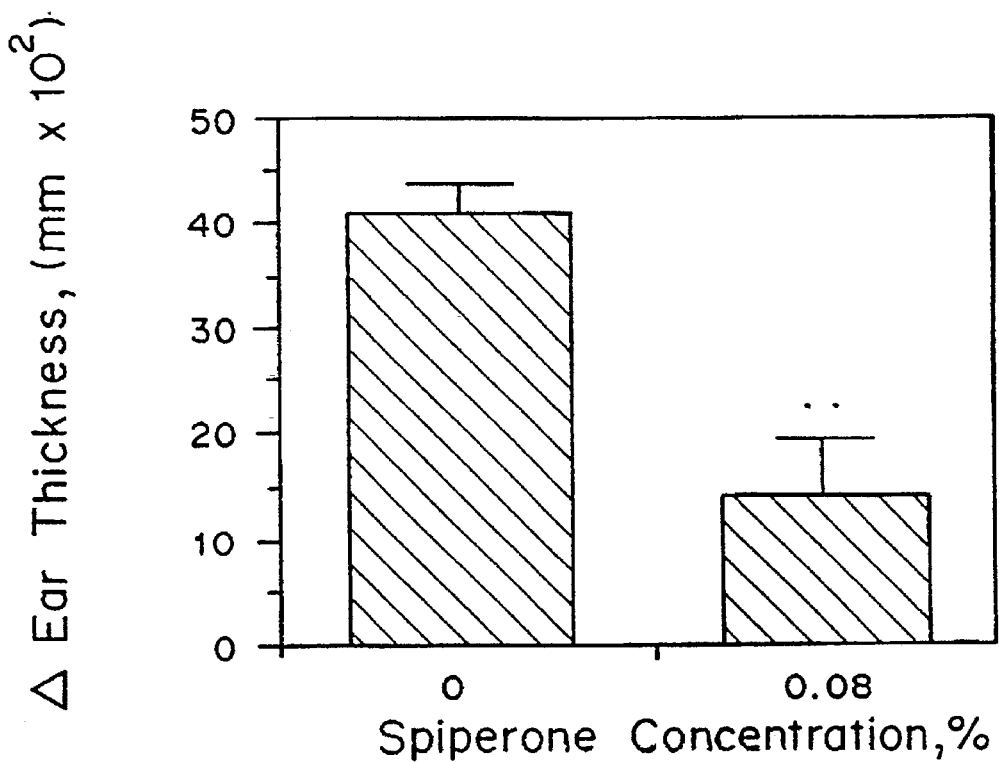
FIG. 5—Effect of spiperone applied topically during the period of sensitization on the tissue swelling associated with oxazolone-induced contact hypersensitivity reactions. Oxazolone was applied to the abdomens of BALB/c mice on day 0. The change in ear thickness was determined 24 hours after challenge with oxazolone on day 6. Treatment with spiperone (50 µl of 0.08% spiperone in propylene glycol) applied to the abdomens on days −2, −1, 0, 1 and 2 significantly diminished contact hypersensitivity reactions in the right ears of the treated animals (**p<0.01 when compared to the right ears in the control mice treated with vehicle).
Figure 6:
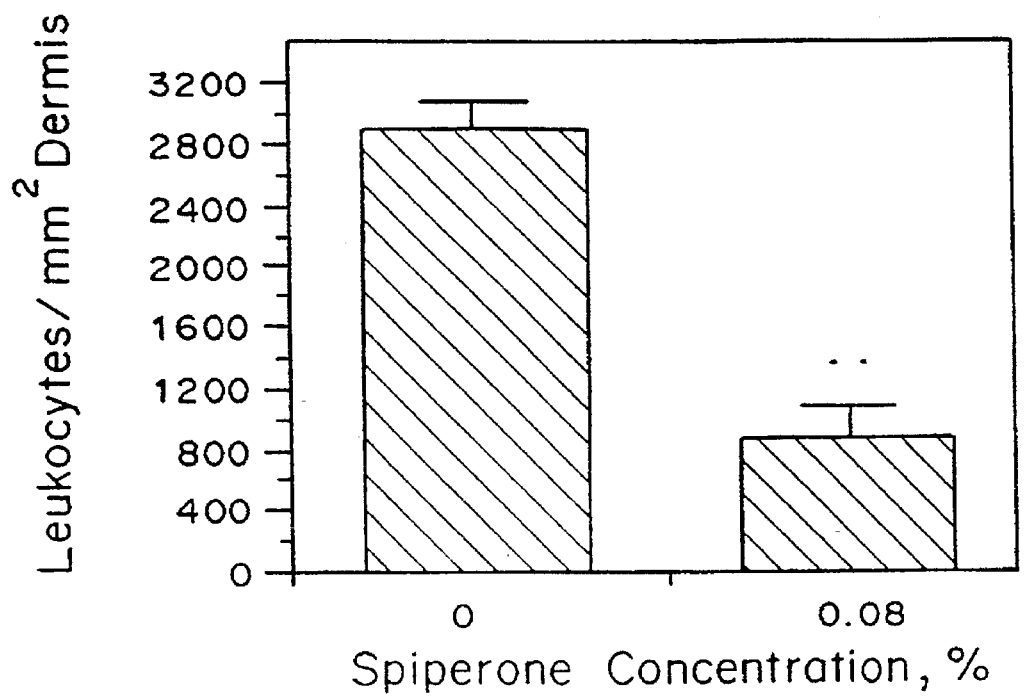
FIG. 6—Effect of spiperone applied topically during the period of sensitization on the leukocyte infiltration associated with oxazolone-induced contact hypersensitivity reactions. These data (mean ±SEM) are from the same mice whose ear thickness measurements are presented in FIG. 5. Topical treatment with spiperone significantly diminished the reactions when compared to those in vehicle-treated mice (**p<0.01).

Effects of Spiperone on the Sensitization Phase of contact Hypersensitivity—For these experiments, mice were treated topically with spiperone in Vehicle-N or Vehicle-N alone, applied to the abdomen beginning two days prior to sensitization and continuing for a total of 5 days (FIGS. 5 and 6). Mice treated with spiperone exhibited 64% less tissue swelling and 70% less leukocyte infiltration at sites of hapten challenge than did vehicle-treated mice (p<0.01 for either comparison). These data show that treatment with topical spiperone can effectively inhibit the sensitization phase of cutaneous contact hypersensitivity.

Figure 7A:
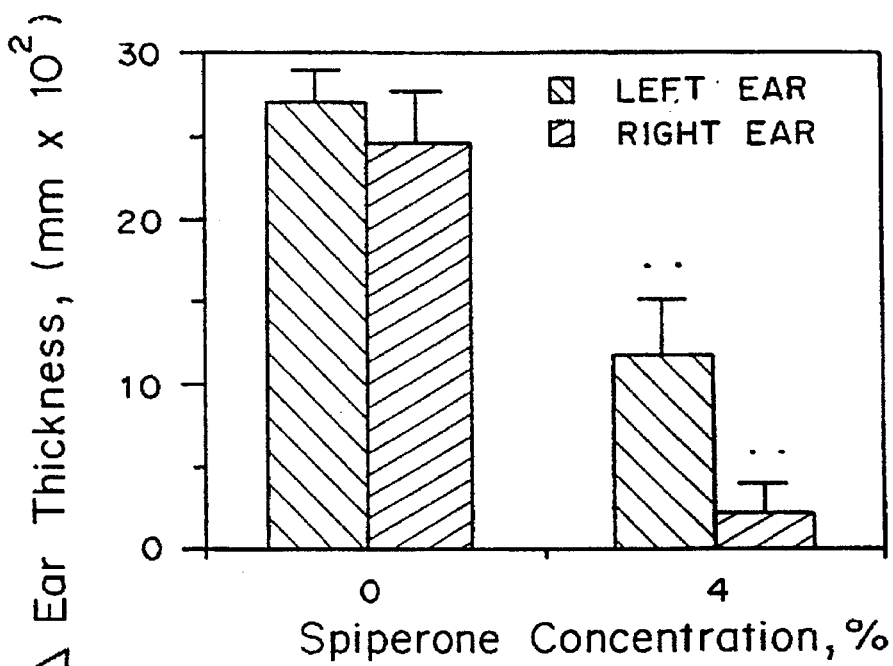
FIGS. 7a,b,c—Effect of topically administered spiperone on tissue swelling associated with oxazolone-induced contact hypersensitivity reactions. Oxazolone was applied to both ears of all mice and the change in ear thickness was measured at a specified interval thereafter. a. One hour after oxazolone challenge, 4.0% spiperone in ethanol:propylene glycol:olive oil was applied to both surfaces of the right ears of some mice, whereas vehicle alone was applied to both surfaces of the right ears of the control (0% spiperone) mice. The ears were measured 24 hours after oxazolone challenge. Local treatment with 4% spiperone suppressed swelling in the treated ear (=p<0.01 vs either contralateral oxazolone treated ears or ears of vehicle treated group) and also diminished the swelling in the contralateral ears (=p<0.01 vs left ears of vehicle treated group), although to a lesser extent than in the treated ears. b. Two hours before oxazolone challenge, 0.13% spiperone in Vehicle-N was applied to both surfaces of the right ears of some mice, whereas vehicle alone was applied to both surfaces of the ears of the control (0% spiperone) animals. The ears were measured 24 hours after oxazolone challenge. Local treatment of the right ear with spiperone significantly suppressed tissue swelling in the treated ear (**p<0.01 vs contralateral oxazolone treated ears or vs right ears of vehicle treated group). However, treatment of the right ear with 0.13% spiperone had no significant effect on the magnitude of swelling in the contralateral oxazolone treated ear. c. Twenty-two hours after oxazolone challenge, 0.13% spiperone in Vehicle-N was applied to both surfaces of the right ears of some mice, whereas vehicle alone was applied to both surfaces of the ears of control (0% spiperone) mice. The change in ear thickness was determined 24 hours after treatment with spiperone, i.e. at 46 hours after challenge with oxazolone. Treatment with spiperone significantly diminished contact hypersensitivity reactions in the right ears of the treated animals (*=p<0.01 when compared to the right ears in the control mice, and p<0.05 when compared to the contralateral ears of the same mice). The reactions in the left ears of the mice treated on the right ears with spiperone were not reduced when compared to reactions in the left ears of the vehicle-treated mice.
Figure 8A:
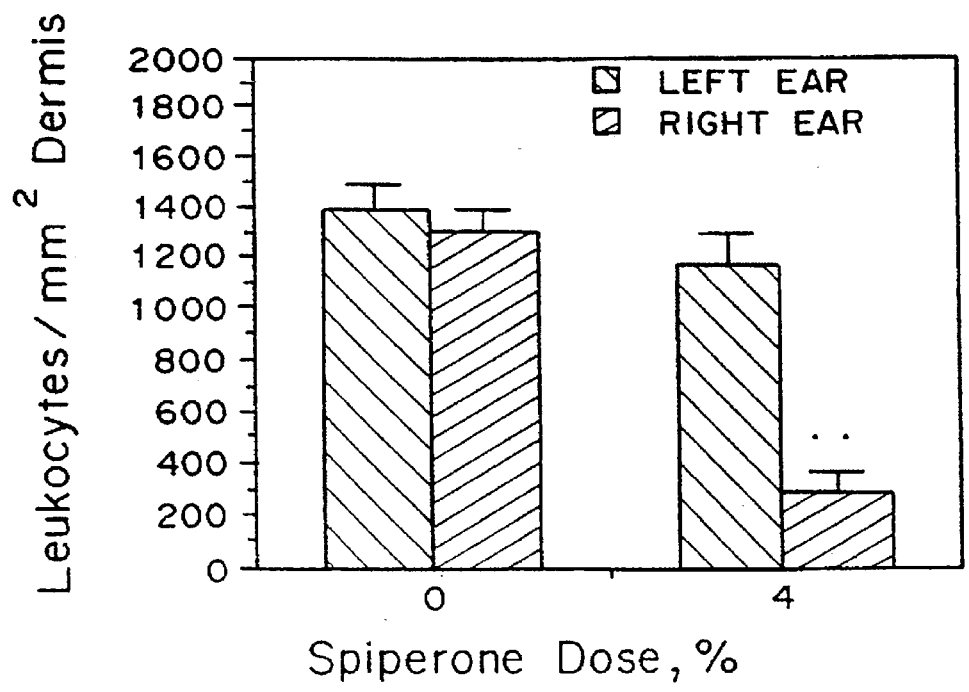
FIGS. 8a,b,c—Effect of topical treatment with spiperone on leukocyte infiltration associated with oxazolone-induced contact hypersensitivity reactions. These data (mean ±SEM) are from the same mice whose ear thickness measurements are presented in FIGS. 7a,b,c. Biopsies were performed 24 hours (a, b) or 46 hours (c) after application of oxazolone. Topical treatment with spiperone significantly diminished the reactions when compared to those in vehicle-treated mice (**=p<0.01).

Effects of Topical Spiperone on Expression of Contact Hypersensitivity—For these experiments, both ears of each mouse were challenged for elicitation of contact hypersensitivity by the application of oxazolone or DNFB (as appropriate) to both surfaces of both ears. Two hours before, one hour after or twenty-two hours after application of hapten, the right ears of some mice were treated with spiperone in vehicle, applied epicutaneously (topically to the skin) to both surfaces of the ears. The right ears of control mice were similarly treated, but with vehicle alone. Topical administration of a 4.0% suspension of spiperone in absolute ethanol, propylene glycol, and olive oil one hour after hapten challenge resulted in a marked diminution of the tissue swelling associated with contact hypersensitivity reactions elicited in the right (spiperone-treated) ear and had a smaller, but nonetheless significant, effect on the swelling associated with the contact hypersensitivity reaction elicited on the contralateral (untreated) ear (FIG. 7a). Thus, reactions in the untreated right ears were 90% smaller than reactions in the right ears of vehicle-treated mice, whereas reactions in the left ears of mice treated on the right ears with spiperone were reduced by 60% compared to the reactions in the right ears of the vehicle-treated mice (FIG. 7a). When the effect on leukocyte infiltration associated with the contact hypersensitivity reactions was assessed (FIG. 8a), the results were similar. Reactions in the spiperone-treated right ears were diminished by 76% compared to the right ears of vehicle-treated mice, whereas reactions in the left ears of mice treated on the right ears with spiperone were reduced only 22% compared to those in the left ears of vehicle-treated mice.

Figure 7B:
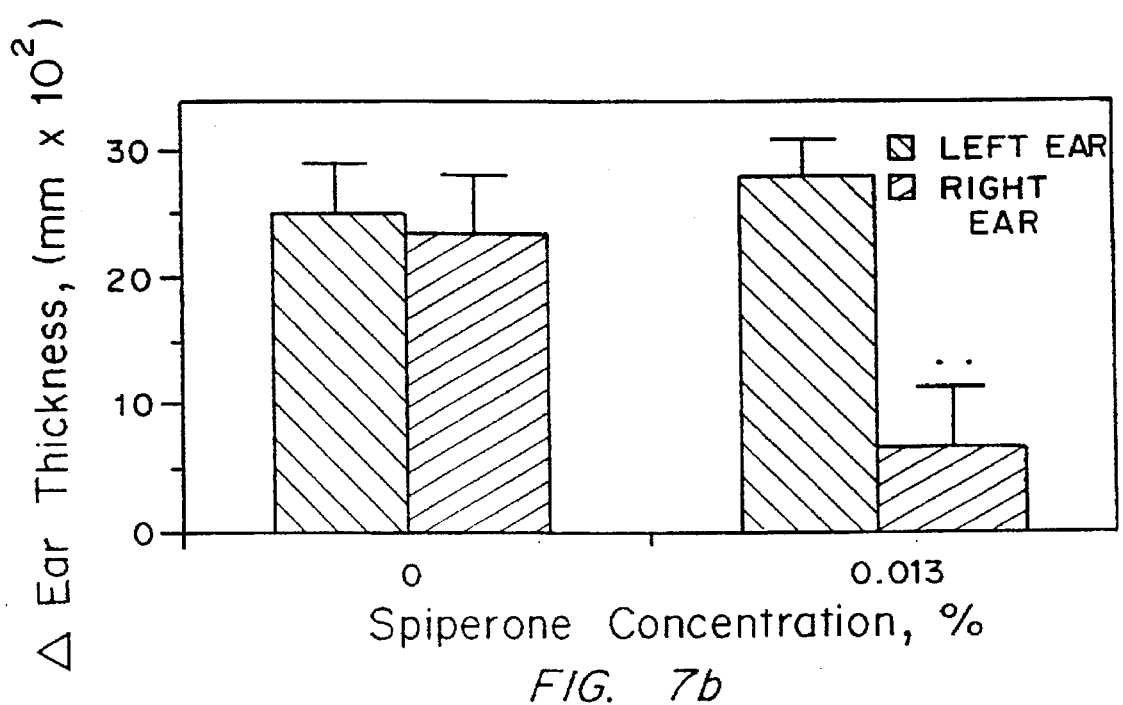
Figure 7C:
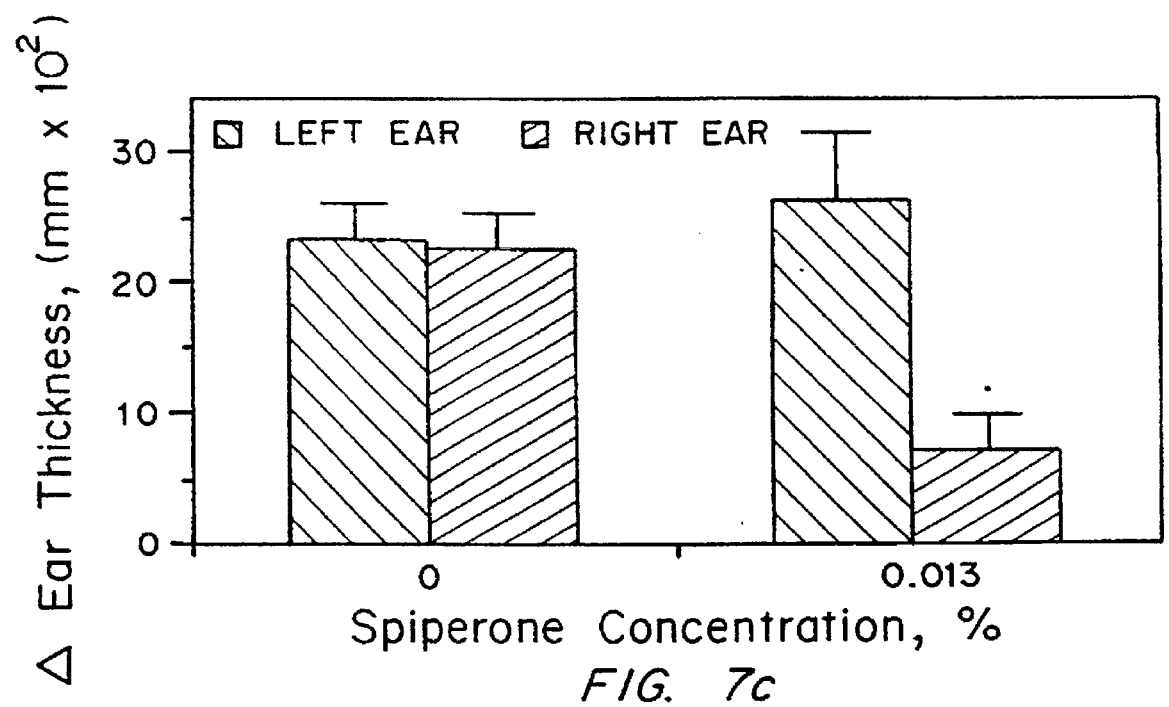
Figure 8B:
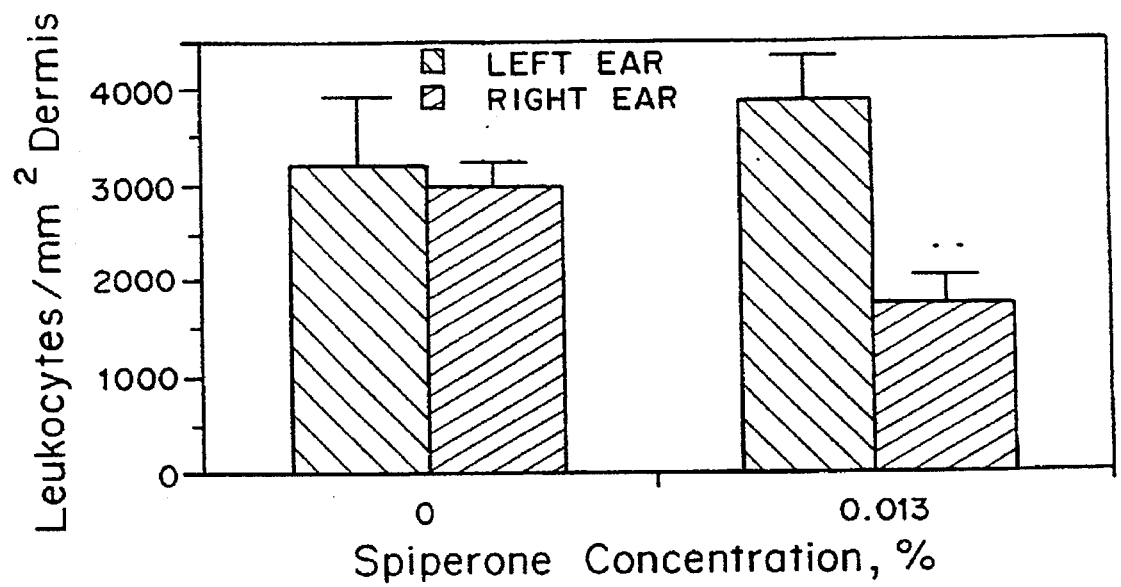
Figure 8C:
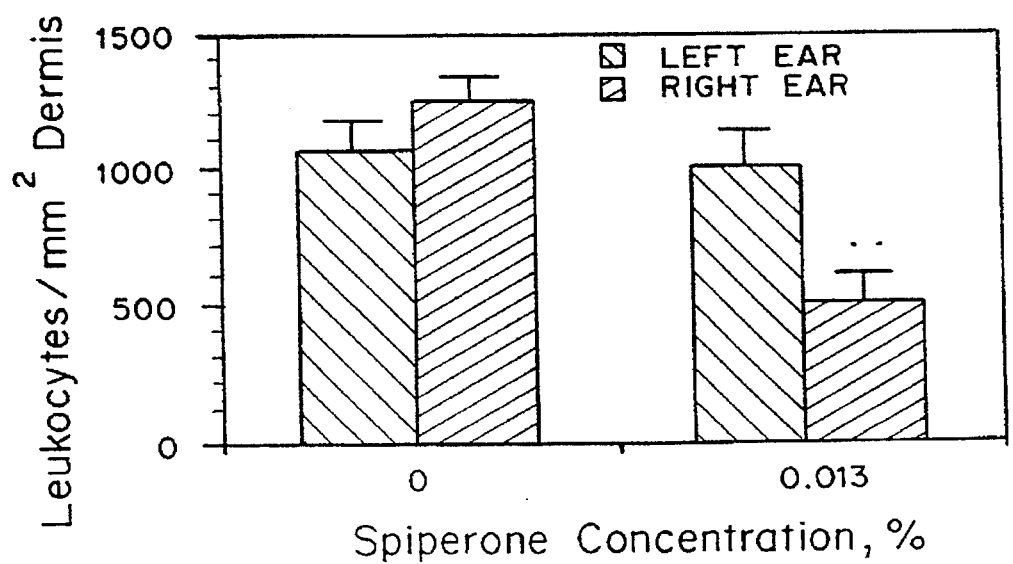

A lower concentration of spiperone, applied topically to the right ear 2 hours before (FIGS. 7b and 8b) or 22 hours after (FIGS. 7c and 8c) hapten challenge was also tested. The results demonstrate that the lower concentration of spiperone inhibited the majority of the tissue swelling and leukocyte infiltration associated with contact hypersensitivity reactions elicited at the site of treatment (the right ear), but had no significant effect on the intensity of the reactions elicited by the same dose of hapten applied to the contralateral (left) ear. Note that treatment with either vehicle had little or no effect on the responses (FIGS. 7 and 8).

Although topical application of spiperone was extremely effective in diminishing both the tissue swelling and the leukocyte infiltration associated with contact hypersensitivity reactions, these effects were observed in the absence of detectable alterations in the behavior of the mice. In contrast to mice treated systemically with spiperone, the mice treated topically with this agent appeared active and retained apparently normal interest in food and water.

Figure 9:
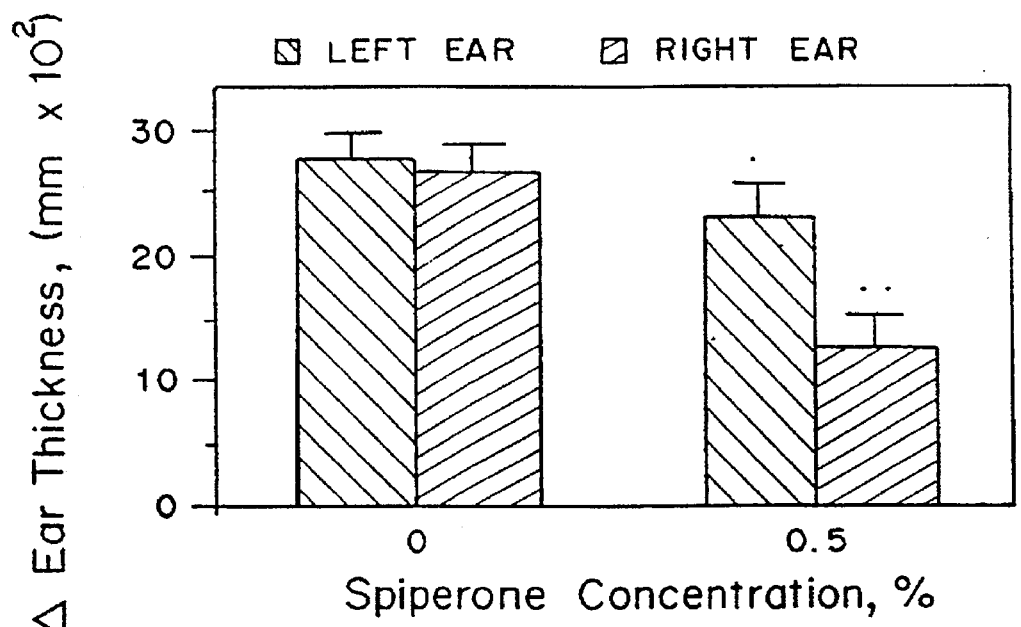
FIG. 9—Effect of topically administered spiperone on tissue swelling associated with DNFB-induced contact hypersensitivity reactions. DNFB was applied to both ears of C57BL/6J mice. One hour later, 0.5% spiperone was applied to both surfaces of the right ears of some mice, whereas vehicle alone was applied to both surfaces of the right ears of the control (0% spiperone) mice. The change in ear thickness was determined 24 hours after challenge with DNFB. Treatment with spiperone significantly diminished contact hypersensitivity reactions in the right ears of the treated animals (**$p<0.01$ when compared to the right ears in the control mice, and $p<0.05$ when compared to the contralateral ears of the same mice). The reactions in the left ears of the mice treated on the right ears with spiperone were also reduced slightly when compared to reactions in the left ears of the vehicle-treated mice (*$p<0.05$).

To evaluate the effect of topical treatment with spiperone on contact hypersensitivity reactions elicited with a different hapten, the effect of topical treatment with a 0.5% suspension of spiperone on the contact hypersensitivity reactions elicited with DNFB was examined. Topical treatment with spiperone significantly diminished the tissue swelling associated with reactions to DNFB (by 45%, FIG. 9) and had an even more significant effect on leukocyte infiltration (a reduction of 71% compared to right ears of vehicle-treated mice, FIG. 10). At this dose of spiperone and with this hapten, the effect of spiperone on reactions elicited in the left ears of mice treated on the right ears with the drug were modest (28% reduction in tissue swelling and 18% reduction in leukocyte infiltration compared to values for the left ears of vehicle-treated mice, FIGS. 9 and 10). In fact, in this experiment, the effect of spiperone applied to the right ears on the leukocyte infiltration associated with reactions elicited in the left ears was not significant ($p > 0.05$).

EXAMPLE 2: Comparison of Immunosuppressant versus Anti-inflammatory activity.

Mice were sensitized to oxazolone as described in Example 1. Three days later, slow release indomethacin pellets (0.05 mg, 3 week release) were implanted subcutaneously under light ether anesthesia. The dose of indomethacin delivered by these pellets has been previously shown to completely block prostaglandin synthesis in mice, by Jun, D. D., et al., *J. Invest. Dermatol.* 90:311 (1988).

Three days later, mice were challenged for contact hypersensitivity as in example 1. When the hypersensitivity response was assessed 24 hours later, by measurements of tissue swelling and leukocyte infiltration, indomethacin was shown to have no significant effect on the response. These data show that a classic anti-inflammatory agent, indomethacin, cannot suppress the immunologically specific oxazolone induced contact hypersensitivity response.

Modifications and variations of the present invention relating to methods for the treatment of pathology associated with immune responses that includes topical administration of an effective amount of spiperone or a spiperone derivative will be obvious to those skilled in the art from the foregoing detailed description of the invention. Such modifications and variations are intended to come within the scope of the appended claims.

We claim:

1. A topical pharmaceutical composition for the treatment of a cutaneous, ocular, or mucosal pathology associated with an immune response in a human or other mammal comprising an effective amount of a compound selected from the group consisting of spiperone or its pharmaceutically acceptable salt, in combination with a pharmaceutically acceptable opthalmic carrier.

2. A topical pharmaceutical composition for the treatment of a cutaneous, ocular, or mucosal pathology associated with an immune response in a human or other mammal comprising an effective amount of spiperone or its pharmaceutically acceptable salt in a pharmaceutically acceptable diluent or carrier, in a time release formulation.

3. A topical pharmaceutical composition for the treatment of a cutaneous, ocular, or mucosal pathology associated with an immune response in a human or other mammal comprising an effective amount of spiperone or its pharmaceutically acceptable salt, wherein the compound in administered via a retention enema.

* * * * *